(12) United States Patent
Bonde-Larsen et al.

(10) Patent No.: US 8,039,672 B2
(45) Date of Patent: Oct. 18, 2011

(54) METHOD OF OBTAINING 3,3-DIPHENYLPROPYLAMINES

(75) Inventors: Antonio Lorente Bonde-Larsen, Valladolid (ES); Pablo Martin Pascual, Valladolid (ES); Jorge Martin Juarez, Valladolid (ES); Miquel Armengol Montserrat, Barcelona (ES)

(73) Assignee: Interquim, S.A., Sant Cugat del Valles (ES)

( * ) Notice: Subject to any disclaimer, the term of this patent is extended or adjusted under 35 U.S.C. 154(b) by 573 days.

(21) Appl. No.: 11/989,962

(22) PCT Filed: Aug. 3, 2006

(86) PCT No.: PCT/ES2006/000458
§ 371 (c)(1),
(2), (4) Date: Dec. 2, 2008

(87) PCT Pub. No.: WO2007/017544
PCT Pub. Date: Feb. 15, 2007

(65) Prior Publication Data
US 2010/0286446 A1  Nov. 11, 2010

(30) Foreign Application Priority Data
Aug. 5, 2005 (ES) .................................. 200501990

(51) Int. Cl.
*C07C 211/00* (2006.01)
(52) U.S. Cl. .......................... 564/316; 564/443; 514/648
(58) Field of Classification Search ........................ None
See application file for complete search history.

(56) References Cited

U.S. PATENT DOCUMENTS 5,922,914 A * 7/1999 Gage et al. .................... 564/413
2010/0234473 A1 * 9/2010 Fischer ......................... 514/648

OTHER PUBLICATIONS

Masuyama et al.,"Animation of Allylic Alcohols with Tin(II) Chloride and Triethelamine", Chemistry Letters, 1995, pp. 1121-1122.

Manninen et al.,"Hydride Transfer Reaction Products in the Aminomethylation of Styrene", Acta Chemica Scandinavica, Series B: Organic Chemistry and Biochemistry, 1995, vol. 40, No. 3, pp. 190-195.

Gomez-Gallego et al.,"On the Reduction of α,β-Unsaturated (Group 6) Carben Complexes by $NaBH_4$", Tetrahedron, 2000, vol. 56, pp. 4893-4905.

Asoyan et al., "Derivatives of arylalkylamines.XXVII. Synthesis and pharmacological activity of several derivatives of [3-(2-hydroxy-5carboxy)phenyl]-3-phenylpropionic acid", Armyanskii Khimicheskii Zhrnal, 1990, vol. 43, No. 11, pp. 719-723.

* cited by examiner

*Primary Examiner* — Sudhakar Katakam
(74) *Attorney, Agent, or Firm* — Birch, Stewart, Kolasch & Birch, LLP

(57) ABSTRACT

The invention relates to a method of obtaining 3,3-diphenyl-propylamines (I), wherein $R_1$ is H, alkyl, haloalkyl or alkoxyalkyl, $R_2$ is alkyl, alkoxy, halogen, $NO_2$, CN, CHO, which may be free or protected, $CH_2OH$ or $COOR_6$, and $R_3$ and $R_4$ are selected independently from H and alkyl or together with the nitrogen to which they are bound form a ring having 3 to 7 members. The inventive method consists in reacting a propylenephenylamine and a disubstituted aromatic hydrocarbon and, if necessary, separating the desired enantiomer or the mixture of enantiomers, and/or converting the compound (I) into a salt. Compounds (I) are muscarinic receptor antagonists which can be used in the treatment of urinary incontinence and other symptoms of urinary bladder hyperactivity. Said compounds include tolterodine.

(I)

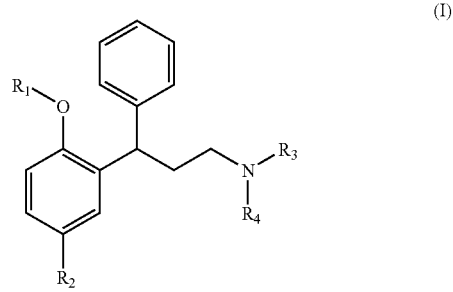

32 Claims, No Drawings

METHOD OF OBTAINING 3,3-DIPHENYLPROPYLAMINES

FIELD OF THE INVENTION

The invention relates to a method of obtaining 3,3-diphenylpropylamines, their enantiomers or mixtures thereof, or their salts, including pharmaceutically acceptable salts.

BACKGROUND OF THE INVENTION 3,3-diphenylpropylamines are known which act as muscarinic receptor antagonists and are useful in the treatment of urinary incontinence and other symptoms of urinary bladder hyperactivity. Said compounds include the compound N,N-diisopropyl-3-(2-hydroxy-5-methylphenyl)-3-phenylpropylamine, the (R) enantiomer of which is tolterodine, the International Nonproprietary Name of the compound (R)-(+)-N,N-diisopropyl-3-(2-hydroxy-5-methylphenyl)-3-phenylpropylamine [(R)-tolterodine]. The (S) enantiomer, (S)-(−)-N,N-diisopropyl-3-(2-hydroxy-5-methylphenyl)-3-phenylpropylamine or (S)-tolterodine, and its use in the treatment of urinary and gastrointestinal disorders has been described in international patent application WO 98/03067. The use of tolterodine and some of its derivatives in the treatment of asthma in mammals has been described in U.S. Pat. No. 6,538,035.

Tolterodine and other 3,3-diphenylpropylamines analogs were first described in U.S. Pat. No. 5,382,600. Said patent described several methods for preparing tolterodine and its analogs generally based on displacing a tosylate with diisopropylamine. Said method has several drawbacks. The displacement reaction occurs very slowly, therefore several days are needed to carry out said reaction, and the total yields are low. Some of the reagents used such as methyl iodide or lithium aluminium hydride are expensive and their use involves a hazard. All this makes the total method expensive and not very productive.

An alternative method of obtaining tolterodine is described in U.S. Pat. No. 5,922,914. Said method comprises reducing 3,4-dihydro-6-methyl-4-phenyl-2H-benzopyran-2-one with DIBAL (diisobutylaluminum hydride) in toluene to give the corresponding hemiketal 6-methyl-4-phenyl-3,4-dihydro-2H-1-benzopyran-2-ol which is then subjected to reductive amination to yield racemic tolterodine. This method also has some drawbacks because the DIBAL reagent is used, which is expensive and hazardous, therefore it is not suitable for being put into practice on an industrial level.

International patent application WO 03/014060 describes a method of obtaining tolterodine which, although it partially solves some drawbacks of the previous methods, still includes problematic steps, particularly obtaining the intermediate 3-(2-methoxy-5-methylphenyl)-3-phenylpropanol, transforming it into the tosylate derivative and subsequently displacing the tosylate with diisopropylamine. These steps still have serious problems, such as the steric hindrance of diisopropylamine in the tosylate displacement reaction, making the nucleophilic substitution reaction difficult, the high temperatures necessary for it, as well as the long reaction times that they comprise, even days.

A different approach for preparing the (R)-tolterodine enantiomer is formed by several enantioselective syntheses such as those described in U.S. Pat. No. 6,310,248 or by Andersson et al. in J. Org. Chem. 1998, 63, 8067-8070, describing methods in which the participation of asymmetry inducers or chiral auxiliaries respectively, which are generally very expensive reagents, is necessary.

An alternative method to tolterodine synthesis which allows reducing the cost of the method and at the same time achieves good yields and the use of less hazardous reagents is described in Spanish patent application ES 2,235,648. This document details obtaining tolterodine by means of a synthetic route comprising a reductive amination reaction between a 3,3-diphenylpropanal derivative and diisopropylamine in the presence of a reducing agent. Nevertheless, obtaining the starting aldehyde requires several synthetic steps considerably lengthening the global method.

It is therefore necessary to solve the problems associated with the methods belonging to the state of the art and to provide an alternative method of obtaining tolterodine and other 3,3-diphenylpropylamines analogs which improves the cost-effectiveness of the process by using more cost-effective reagents and starting materials which further allow reducing the number of steps of the synthetic route leading to obtaining it. Said method must advantageously be applicable on an industrial level and must provide the desired product with a good yield and quality.

SUMMARY OF THE INVENTION

The invention faces the problem of providing an alternative method of obtaining 3,3-diphenylpropylamines, and particularly tolterodine, which overcomes the problems existing in the different aforementioned state of the art syntheses.

The solution provided by the invention is based on the fact that the inventors have observed that it is possible to obtain 3,3-diphenylpropylamines of formula (I) (defined below), their enantiomers or mixtures thereof, their solvates, hydrates or their salts (including the pharmaceutically acceptable salts and the pharmaceutically unacceptable salts), from the reaction of a propylenephenylamine of formula (II) (defined below) with a disubstituted aromatic hydrocarbon of formula (III) (defined below), by means of a Friedel-Crafts type aromatic electrophilic substitution reaction, providing said compounds with very good yields. Said compound of formula (II) can be obtained from commercial and cost-effective starting compounds.

A method such as that provided by the present invention has the advantage that the number of synthetic steps is considerably reduced compared to the methods of the state of the art, while at the same time high yields with very simple steps are achieved. Likewise, said method is not toxic and allows starting from inexpensive and non-hazardous reagents, providing 3,3-diphenylamines, and, particularly, N,N-diisopropyl-3-(2-hydroxy-5-methylphenyl)-3-phenylpropyl-amine, their enantiomers or mixtures thereof, their solvates, hydrates or their salts, particularly their pharmaceutically acceptable salts, with a good yield and pharmaceutical quality. All this contributes to reducing the global cost of the method, making said method commercially interesting and allowing it to be put into practice on an industrial level.

Therefore, in one aspect, the invention relates to a method of obtaining 3,3-diphenylpropylamines of formula (I), which comprises reacting a propylenephenylamine of formula (II) with a disubstituted aromatic hydrocarbon of formula (III), and then, if desired, separating the desired (R) or (S) enantiomer or the mixture of enantiomers, and/or converting the compound of formula (I) into a salt thereof.

The compound of formula (II), useful in the synthesis of the compound of formula (I), can be easily obtained from commercial and cost-effective starting compounds. Therefore, in another aspect, the invention relates to a method of obtaining 3,3-diphenylamines of formula (I) from a compound of formula (II) obtained by means of a method comprising the reaction between a compound of formula (IV) (defined below) with a primary or secondary amine of formula (V) (defined below) by means of a nucleophilic substitution reaction.

The method of obtaining said compound of formula (II) is an additional object of this invention.

In another aspect, the invention relates to acid addition salts of the compound of formula (II).

DETAILED DESCRIPTION OF THE INVENTION

In one aspect, the invention relates to a method, hereinafter method of the invention [1], of obtaining a 3,3-diphenylpropylamine of formula (I):

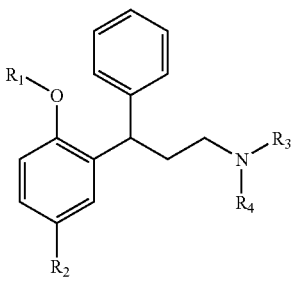

(I)

wherein
$R_1$ is hydrogen, $C_1$-$C_6$ alkyl, $C_1$-$C_6$ haloalkyl or alkoxyalkyl of formula
—$(CH_2)_n$—O—$R_5$, wherein n is an integer comprised between 1 and 3 and $R_5$ is $C_1$-$C_6$ alkyl;
$R_2$ is $C_1$-$C_6$ alkyl, $C_1$-$C_6$ alkoxy, halogen, $NO_2$, CN, CHO which may be free or protected, $CH_2OH$ or $COOR_6$, wherein $R_6$ is H or a $C_1$-$C_6$ alkyl group;
$R_3$ and $R_4$ are selected independently from H and $C_1$-$C_8$ alkyl or together with the nitrogen to which they are bound form a ring having 3 to 7 members;
its enantiomers or mixtures thereof, its solvates, hydrates, or salts,
which comprises:
a) reacting a compound of formula (II)

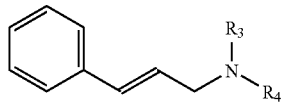

(II)

wherein $R_3$ and $R_4$ have the previously indicated meaning,
with a compound of formula (III)

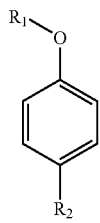

(III)

wherein $R_1$ and $R_2$ have the previously indicated meaning; and
b) if desired, separating the desired (R) or (S) enantiomer, or the mixture of enantiomers, and/or converting the compound of formula (I) into a salt thereof.

As used herein, the term "haloalkyl" relates to a linear or branched alkyl group substituted with one or more halogens such as fluorine, chlorine, bromine or iodine.

The term "protected CHO" relates to a carbonyl group functionalized or protected by groups commonly used to block the functionality of said carbonyl group while other functional groups of the compound react. Said groups can optionally be eliminated to unmask the carbonyl group. Suitable protective groups for a carbonyl group are known in the state of the art and include those described in Green, T. W., "Protective Groups in Organic synthesis" John Wiley & Sons, New York 1999. Examples of protective groups for a carbonyl group include, among others, an ester such as an alkyl ester, methyl ester, ethyl ester, tert-butyl ester or benzyl ester for example, an alkoxy group such as dimethoxy, diethoxy or another $C_1$-$C_6$ dialkoxy, diphenoxy, cyclic ketals such as dioxolanes, 1,3-dioxanes or catechols.

The product of formula (II) can be obtained by methods described in the state of the art or by means of an alternative method provided by this invention which will be described in detail below. The compounds of formula (III) are known and are commercially available.

The reaction of the propylenephenylamine of formula (II) with the disubstituted aromatic hydrocarbon of formula (III) is a Friedel-Crafts type electrophilic substitution reaction of the ortho position of the aromatic ring present in the compound of formula (III), and is carried out in a reaction medium comprising an acid acting as a catalyst of said Friedel-Crafts type aromatic electrophilic substitution reaction. Virtually any type of acid can be used to carry out this reaction. This reaction generally takes place with a high yield, typically comprised between 85% and 90%, thus contributing to the high global yield of the method of obtaining the compound of formula (I) provided by this invention.

In a particular embodiment, said acid is an inorganic acid. Illustrative non-limiting examples of inorganic acids which can be used include hydrobromic, perchloric, sulfuric, hydrochloric, phosphoric acid, etc., and mixtures thereof. Said inorganic acids can be used in the form of aqueous suspension or solutions.

In another particular embodiment, said acid is an organic acid, advantageously a strong organic acid. Illustrative non-limiting examples of organic acids which can be used include sulfonic acids, such as p-toluenesulfonic acid, methanesulfonic acid, etc., acetic acid, trifluoroacetic acid, etc., or mixtures thereof.

In another particular embodiment, the reaction medium comprises one or more inorganic acids and one or more organic acids. Illustrative non-limiting examples of said inorganic and organic acids which can be used have already been mentioned above. In a particular embodiment, the reaction medium comprises an inorganic acid selected from the group consisting of hydrobromic acid, perchloric acid, sulfuric acid, hydrochloric acid, phosphoric acid and mixtures thereof and an organic acid such as acetic acid, for example.

In another particular embodiment, said acid is a Lewis acid such as, for example, $AlCl_3$, $SnCl_4$, $ZnCl_2$, $BF_3$, etc., or mixtures thereof.

The aromatic electrophilic substitution reaction can be carried out in different conditions depending on the reactivity of the compound of formula (III).

When $R_1$ in the compound of formula (III) is hydrogen, the aromatic electrophilic substitution reaction can be carried out in several ways, for example:
using between 1 and 4 equivalents of the derived phenol of formula (III) [$R_1$=H] per equivalent of compound of formula (II) in a reaction medium comprising an inorganic acid, for example aqueous hydrobromic, perchloric, sulfuric, hydrochloric, phosphoric acid or mixtures thereof, and optionally, an organic acid, acetic acid for example, at a temperature comprised between 60° C. and the reflux temperature, preferably between 80° C. and the reflux temperature; or using a Lewis acid, in which case, this aromatic electrophilic substitution reaction can preferably be carried out using between 1 and 4 equivalents of the derived phenol of formula (III) [$R_1$=H] per equivalent of compound of formula (II) in a reaction medium comprising, in addition to a Lewis acid, an organic solvent such as dichloromethane, 1,2-dichloroethane, acetic acid, etc., at a temperature comprised between room temperature (typically between 18° C. and 22° C.) and the reflux temperature, preferably between room temperature and 60° C.; $AlCl_3$ can preferably be used as a Lewis acid, although other Lewis acids, e.g., $SnCl_4$, $ZnCl_2$, $BF_3$, etc. can be used; or using between 1 and 4 equivalents of the derived phenol of formula (III) [$R_1$=H] per equivalent of compound of formula (II) in a reaction medium comprising an organic acid, for example, trifluoroacetic acid, p-toluenesulfonic acid, methanesulfonic acid, etc., and optionally a solvent with a high boiling point, such as toluene, xylene, etc., and/or another (organic or inorganic) acid, acetic acid for example, at a temperature comprised between room temperature (typically between 18° C. and 22° C.) and the reflux temperature, preferably between 40° C. and the reflux temperature.

When $R_1$ in the compound of formula (III) is different from hydrogen, i.e., $C_1$-$C_6$ alkyl or $C_1$-$C_6$ haloalkyl, or alkoxyalkyl of formula —$(CH_2)_n$—O—$R_5$, wherein n and $R_5$ are those defined above, the aromatic electrophilic substitution reaction can be carried out in different ways, for example:

using between 4 and 16 equivalents of the derived alkoxy of formula (III) [$R_1$≠H] per equivalent of compound of formula (II), in a reaction medium comprising an inorganic acid (except hydrobromic acid), for example, generally aqueous perchloric, sulfuric, hydrochloric, phosphoric acid or mixtures thereof, at a temperature comprised between 80° C. and the reflux temperature, preferably at the reflux temperature; or using between 4 and 16 equivalents of the derived alkoxy of formula (III) [$R_1$≠H] per equivalent of compound of formula (II), in a reaction medium in which said compound of formula (II) also acts as a solvent, and comprises a Lewis acid, e.g., $AlCl_3$, $SnCl_4$, $ZnCl_2$, $BF_3$, etc., at a temperature comprised between 20° C. and 100° C., preferably between 40° C. and 60° C.; or using between 4 and 12 equivalents of the derived alkoxy of formula (III) [$R_1$≠H] per equivalent of compound of formula (II), and an organic acid, for example, toluenesulfonic acid, methanesulfonic acid; etc., and, optionally another or other organic acids) e.g., acetic acid, etc., at a temperature comprised between 80° C. and the reflux temperature, preferably between 100° C. and the reflux temperature.

The compound of formula (I) has a chiral carbon and it therefore exists in the form of its isolated (R) or (S) enantiomers or in the form of mixtures of said enantiomers. As used in this description, the term "mixtures of enantiomers" or "enantiomeric mixtures" includes both racemic mixtures and mixtures enriched in any one of the enantiomers. The obtained (R) and (S) enantiomers of the compound of formula (I) can be separated by conventional methods for resolving mixtures of enantiomers, for example, by means of fractional distillation, conventional chromatographic methods, etc. In a particular embodiment, the compound of formula (I) obtained by means of the method provided by this invention is obtained in the form of a mixture of enantiomers, in the form of a racemic mixture, for example. Therefore, if desired, the mixture of enantiomers obtained can be resolved into its corresponding enantiomers to obtain the desired enantiomer. In a particular embodiment, said enantiomer is the enantiomer (R) [(+)-N,N-diisopropyl-3-(2-hydroxy-5-methylphenyl)-3-phenylpropylamine], or tolterodine, also known as (R)-tolterodine, and is pharmaceutically useful. In another particular embodiment, said enantiomer is the enantiomer (S) [(−)-N,N-diisopropyl-3-(2-hydroxy-5-methylphenyl)-3-phenylpropylamine], or (S)-tolterodine, which also has therapeutic applications.

The mixture of enantiomers can be resolved by any conventional method, for example, by using chiral chromatographic columns or by means of fractional crystallization of salts of the enantiomers corresponding with the suitable (chiral) optically active acids. In a particular embodiment, the (R) enantiomer of the compound of formula (I) is separated by means of optical resolution by treating the mixture of enantiomers with L-tartaric acid. The (R)-tolterodine L-tartrate salt or any another salt corresponding with a suitable chiral acid can be crystallized as many times needed until obtaining the (R) enantiomer of the compound of formula (I) with the desired purity. Likewise, if desired, the obtained enantiomer can be transformed into a salt, such as into a pharmaceutically acceptable salt or into a pharmaceutically unacceptable salt thereof by means of conventional methods known by persons skilled in the art.

The compound of formula (I) is an amine and can form addition salts with organic or inorganic acids when it reacts with the suitable acids. Said salts include both pharmaceutically acceptable salts and salts that are not pharmaceutically acceptable (i.e., pharmaceutically unacceptable salts), which can occasionally be useful in the synthesis, isolation or purification of the desired compound of formula (I) or of the pharmaceutically desired salt. Illustrative non-limiting examples of said salts include hydrochloride, hydrobromide, sulfate, methanesulfonate, phosphate, nitrate, benzoate, citrate, tartrate, fumarate, maleate, although they are not limited thereto. Said salts can be obtained by conventional methods by reacting the free amine with the acid in question. In a particular embodiment, said salt is a pharmaceutically acceptable salt, hydrobromide or tartrate, for example. Said salt can be obtained by the reaction of the free amine with hydrobromic acid or as a result of carrying out the addition reaction by treatment with hydrobromic acid in the presence of acetic acid, or by the reaction with tartaric acid. If desired, said addition salt can optionally be transformed into the corresponding free amine by conventional methods, by varying the pH of a solution comprising said salt until obtaining the free amine, for example.

The compound of formula (I) can be obtained in free base or in salt form. In both cases, it can be obtained in crystalline form, both as free compounds and as solvates (for example hydrates), both forms being included within the scope of the present invention. The solvation methods are generally known in the state of the art.

The method of the invention [1] provides compounds of formula (I), their enantiomers, hydrates, solvates and salts. In a particular embodiment, said method provides compounds of formula (I) wherein $R_1$ is H or methyl, $R_2$ is methyl and $R_3$ and $R_4$ are both isopropyl, preferably compounds of formula (I) wherein $R_1$ is H, $R_2$ is methyl and $R_3$ and $R_4$ are both isopropyl, as well as their enantiomers or mixtures thereof and their salts (including the pharmaceutically acceptable salts and the pharmaceutically unacceptable salts). In a particular embodiment, said method provides the compound N,N-diisopropyl-3-(2-methoxy-5-methylphenyl)-3-phenylpropylamine, its enantiomers or its salts. In a specific preferred embodiment, the method of the invention [1] provides the compound (R)-(+)-N,N-diisopropyl-3-(2-methoxy-5-methylphenyl)-3-phenylpropylamine or a salt thereof, such as the hydrobromide or tartrate.

In another aspect, the invention relates to a method of obtaining a 3,3-diphenylpropylamine of formula (I')

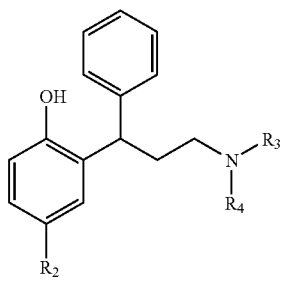

wherein
$R_2$ is $C_1$-$C_6$ alkyl, $C_1$-$C_6$ alkoxy, halogen, $NO_2$, CN, CHO which may be free or protected, $CH_2OH$ or $COOR_6$, wherein $R_6$ is H or $C_1$-$C_6$ alkyl;
$R_3$ and $R_4$ are selected independently from H, $C_1$-$C_6$ alkyl, or together with the nitrogen to which they are bound form a ring having 3 to 7 members;
its enantiomers or mixtures thereof, its solvates, hydrates, or salts,
which comprises:
a) reacting a compound of formula (II)

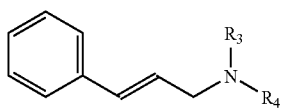

wherein $R_3$ and $R_4$ have the previously indicated meaning,
with a compound of formula (III')

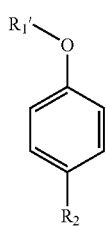

wherein
$R'_1$ is $C_1$-$C_6$ alkyl, $C_1$-$C_6$ haloalkyl or alkoxyalkyl of formula
—$(CH_2)_n$—O—$R_5$, wherein n is an integer comprised between 1 and 3 and $R_5$ is $C_1$-$C_6$ alkyl; and
$R_2$ has the previously indicated meaning, to give rise to a compound of formula (I"):

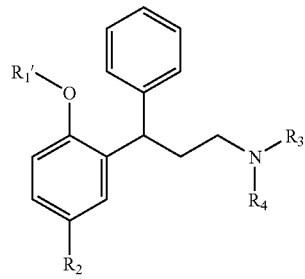

wherein $R'_1$, $R_2$, $R_3$ and $R_4$ have the previously indicated meaning;
b) transforming $R'_1$, into hydrogen to obtain the compound of formula (I'); and
c) if desired, separating the desired (R) or (S) enantiomer, or the mixture of enantiomers, and/or converting the compound of formula (I') into a salt thereof.

The product of formula (II) can be obtained by methods described in the state of the art or by means of an alternative method provided by this invention which will be described in detail below. The compounds of formula (III') are known and are commercially available.

The reaction of the propylenephenylamine of formula (II) with the disubstituted aromatic hydrocarbon of formula (III') is a Friedel-Crafts type electrophilic substitution reaction of the ortho position of the aromatic ring present in the compound of formula (III') and is carried out in a reaction medium comprising an acid acting as a catalyst of said Friedel-Crafts type aromatic electrophilic substitution reaction. Nevertheless, unlike the method of the invention [1], in this method this step cannot be carried out by using aqueous hydrobromic acid given that it would dealkylate the alkoxide group of the molecule, therefore other acids are used, for example, aqueous inorganic acids such as sulfuric, perchloric acid, etc., and mixtures thereof; organic acids such as the p-toluenesulfonic acid, methanesulfonic acid, trifluoroacetic acid, etc., and mixtures thereof, or Lewis acids such as $AlCl_3$, $SnCl_4$, $ZnCl_2$, $BF_3$, etc.

In a particular embodiment, said acid is an inorganic acid except for hydrobromic acid due to the reasons mentioned above. Illustrative non-limiting examples of inorganic acids which can be used include generally aqueous perchloric, sulfuric acids, etc., and mixtures thereof.

In another particular embodiment, said acid is an organic acid, advantageously a strong organic acid. Illustrative non-limiting examples of organic acids which can be used include sulfonic acids such as the p-toluenesulfonic, methanesulfonic acid, etc., acetic acid, trifluoroacetic acid, etc., or mixtures thereof.

In another particular embodiment, the reaction medium comprises one or more inorganic acids, except hydrobromic acid, and one or more organic acids. Illustrative non-limiting examples of said inorganic and organic acids which can be used have already been mentioned above. In a particular embodiment, the reaction medium comprises an inorganic acid selected from the group consisting of perchloric acid, sulfuric acid and mixtures thereof, and an organic acid such as acetic acid, for example.

In another particular embodiment, said acid is a Lewis acid such as, for example, $AlCl_3$, $SnCl_4$, $ZnCl_2$, $BF_3$, etc., or mixtures thereof.

The aromatic electrophilic substitution reaction can be carried out in different conditions depending on the reactivity of the compound of formula (III'). By way of illustration, said aromatic electrophilic substitution reaction can be carried out:

using between 4 and 16 equivalents of the derived alkoxy of formula (III') per equivalent of compound of formula (II) in a reaction medium comprising a generally aqueous inorganic acid (except hydrobromic acid), for example, sulfuric, perchloric acid, etc., at a temperature comprised between 80° C. and the reflux temperature, preferably at the reflux temperature; or using between 4 and 16 equivalents of the derived alkoxy of formula (III') per equivalent of compound of formula (II), which can also act as a solvent, in a reaction medium comprising a Lewis acid, e.g., $AlCl_3$, $SnCl_4$, $ZnCl_2$, $BF_3$, etc., at a temperature comprised between 20° C. and 100° C., preferably between 40° C. and 60° C.; or using from 4 to 12 equivalents of the derived alkoxy of formula (III') per equivalent of compound of formula (II) and an organic acid, for example, toluenesulfonic, methanesulfonic acid, etc., and, optionally another or other organic acids, e.g. acetic acid, etc., at a temperature comprised between 80° C. and the reflux temperature, preferably at 100° C. and the reflux temperature.

Step b) of transforming $R'_1$ [$C_1$-$C_6$alkyl, $C_1$-$C_6$ haloalkyl or —$(CH_2)_n$—O—$R_5$ alkoxyalkyl] into hydrogen can be carried out by means of any method known in the state of the art; nevertheless, in a particular embodiment, said transformation is carried out by means of a dealkylation reaction by treating the compound with an acid, for example, with aqueous hydrobromic acid, optionally together with an organic acid such as acetic acid. In a particular embodiment, the dealkylation reaction is carried out by treating with a mixture of aqueous hydrobromic acid and acetic acid.

The compound of formula (I') has a chiral carbon and therefore exists in the form of its isolated (R) or (S) enantiomers or in the form of mixtures of said enantiomers. The obtained (R) and (S) enantiomers of the compound of formula (I') can be separated by conventional methods for resolving mixtures of enantiomers, for example, by means of fractional distillation, conventional chromatographic methods, etc. In a particular embodiment, the compound of formula (I') obtained by means of the method provided by this invention is obtained in the form of a mixture of enantiomers, in the form of a racemic mixture, for example. Therefore, if desired, the mixture of enantiomers obtained can be resolved into its corresponding enantiomers to obtain the desired enantiomer. In a particular embodiment, said enantiomer is the (R) enantiomer [(R)-(+)-N,N-diisopropyl-3-(2-hydroxy-5-methylphenyl)-3-phenylpropylamine], or tolterodine, also known as (R)-particular embodiment, said enantiomer is the (S) enantiomer [(S)-(–)-N,N-diisopropyl-3-(2-hydroxy-5-methylphenyl)-3-phenylpropylamine], or (S)-tolterodine, which also has therapeutic applications.

The mixture of enantiomers can be resolved by any conventional method, for example, by using chiral chromatographic columns or by means of fractional crystallization of salts of the enantiomers corresponding with the suitable (chiral) optically active acids. In a particular embodiment, the (R) enantiomer of the compound of formula (I') is separated by means of optical resolution by treating the mixture of enantiomers with L-tartaric acid. The (R)-tolterodine L-tartrate salt or any another salt corresponding with a suitable chiral acid can be crystallized as many times needed until obtaining the (R) enantiomer of the compound of formula (I') with the desired purity. Likewise, if desired, the obtained enantiomer can be transformed into a pharmaceutically acceptable salt thereof by means of conventional methods known by persons skilled in the art.

The compound of formula (I') is an amine and can form addition salts with organic or inorganic acids when it reacts with the suitable acids. Said salts include both pharmaceutically acceptable salts and salts that are not pharmaceutically acceptable, which can occasionally be useful in the synthesis, isolation or purification of the desired compound of formula (I') or of the pharmaceutically desired salt. Illustrative non-limiting examples of said salts include hydrochloride, hydrobromide, sulfate, methanesulfonate, phosphate, nitrate, benzoate, citrate, tartrate, fumarate, maleate, although they are not limited thereto. Said salts can be obtained by conventional methods by reacting the free amine with the acid in question. In a particular embodiment, said salt is a pharmaceutically acceptable salt, hydrobromide or tartrate, for example. Said salt can be obtained by the reaction of the free amine with hydrobromic acid or as a result of carrying out the addition reaction by treatment with hydrobromic acid in the presence of acetic acid, or by the reaction with tartaric acid. If desired, said addition salt can optionally be transformed into the corresponding free amine by conventional methods, by varying the pH of a solution comprising said salt until obtaining the free amine, for example.

The compound of formula (I') can be obtained in free base or in salt form. In both cases, it can be obtained in crystalline form, both as free compounds and as solvates (for example hydrates), both forms being included within the scope of the present invention. The solvation methods are generally known in the state of the art.

This method provides compounds of formula (I'), its enantiomers, hydrates, solvates and salts. In a particular embodiment, said method provides compounds of formula (I') wherein $R_2$ is methyl and $R_3$ and $R_4$ are both isopropyl, as well as their enantiomers or mixtures thereof and their salts (including the pharmaceutically acceptable salts and the pharmaceutically unacceptable salts). In a particular embodiment, said method provides the compound N,N-diisopropyl-3-(2-methoxy-5-methylphenyl)-3-phenylpropylamine, its enantiomers or its salts. In a specific preferred embodiment, this method provides the compound (R)-(+)-N,N-diisopropyl-3-(2-methoxy-5-methylphenyl)-3-phenylpropylamine or a salt thereof, such as hydrobromide or tartrate.

The compound of formula (II), the starting product of the method of the invention or of the compound of formula (I'), can be obtained by means of a method which comprises reacting a compound of formula (IV)

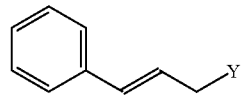

(IV)

wherein Y is a leaving group,
with a primary or secondary amine of formula (V)

(V)

wherein $R_3$ and $R_4$ are selected independently from hydrogen and linear or branched $C_1$-$C_8$ alkyl or together with the nitrogen to which they are bound form a ring having 3 to 7 members.

This reaction consists of a nucleophilic substitution of the leaving group Y by an amine of formula (V), which is in a proportion varying between 1 and 8 equivalents, preferably between 2 and 6 equivalents, per equivalent of compound of formula (IV). Although compounds of formula (IV) having any leaving group, advantageously any good leaving group, could be used, it is preferred that Y is a halogen, a tosylate or a mesylate, Y is preferably Br or Cl and, for cost-effectiveness reasons, it is preferred that Y is Cl. The reaction is carried out in a solvent. Alcohols, toluene, xylene, acetonitrile, acetone, dimethylformamide (DMF), 1,2-dichloroethane, etc., preferably alcohols, toluene or xylene, even more preferably alcohols with five or less carbon atoms, for example, ethanol or isopropanol, preferably ethanol, can be used as solvents. The reaction is carried out at a temperature comprised between room temperature (typically between 18° C. and 22° C.) and the reflux temperature, preferably between 30° C. and 78° C., even more preferably between 40° C. and 70° C.

In the particular case of using alcohol solvents, e.g., ethanol or isopropanol, the reaction is carried out at a temperature comprised between 0° C. and the boiling temperature of the solvent. In turn, when toluene or xylene are used as solvents, the reaction is carried out at a temperature comprised between 80° C. and the boiling temperature of the solvent.

The state of the art describes obtaining compounds comprised within formula (II) by means of a starting reactant such as the compound of formula (IV) containing an OH group as a leaving group (Masuyama, Y. et al., *Chemistry Lett.*, 1995, 12, 1120); nevertheless, the action of a catalyst such as Pd(PPh$_3$)$_4$ in the presence of SnCl$_2$ is necessary to prevent the amine from reacting with the double bond. Unlike what could be expected, in the method of obtaining the compound of formula (II) provided by this invention, the primary or secondary amine of formula (V) does not attack the double bond of the propene part but rather substitutes the leaving group Y without the presence of any compound deactivating said double bond being necessary.

In a particular embodiment, this method allows obtaining compounds of formula (II) wherein $R_3$ and $R_4$ are both isopropyl.

The compound of formula (II) is an amine and can form addition salts with organic or inorganic salts when it reacts with the suitable acids. Illustrative non-limiting examples of said salts include hydrochloride, hydrobromide, sulfate, methanesulfonate, phosphate, nitrate, benzoate, citrate, tartrate, fumarate, maleate, although they are not limited thereto. Said salts can be obtained by conventional methods by reacting the free amine with the acid in question. If desired, said addition salt can optionally be transformed into the corresponding free amine by conventional methods, by varying the pH of a solution comprising said salt until obtaining the free amine, for example.

The acid addition salts of the compound of formula (II) are in themselves an additional aspect of the present invention. Therefore, in another aspect, the invention relates to an acid addition salt of a compound of formula (II) comprising said compound of formula (II) and an acid. Said acid can be an organic or inorganic acid. By way of a non-hydrochloride, hydrobromide, sulfate, methanesulfonate, phosphate, nitrate, benzoate, citrate, tartrate, fumarate, maleate, etc. In a particular embodiment, $R_3$ and $R_4$ are both isopropyl. In another particular embodiment, said salt is the hydrochloride or hydrobromide of the compound of formula (II), preferably N,N-diisopropyl-3-phenyl-2-propenamine hydrochloride or N,N-diisopropyl-3-phenyl-2-propenamine hydrobromide.

In another aspect, the invention relates to a method, hereinafter method of the invention [2], of obtaining a 3,3-diphenylpropylamine of formula (I):

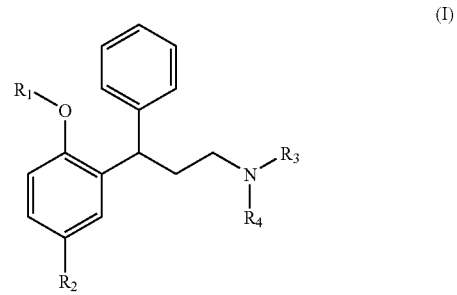

(I)

wherein
$R_1$ is $C_1$-$C_6$ alkyl, $C_1$-$C_6$ haloalkyl or alkoxyalkyl of formula
—(CH$_2$)$_n$—O—R$_5$, wherein n is an integer comprised between 1 and 3 and $R_5$ is $C_1$-$C_6$ alkyl;
$R_2$ is $C_1$-$C_6$ alkyl, $C_1$-$C_6$ alkoxy, halogen, NO$_2$, CN, CHO which may be free or protected, CH$_2$OH or COOR$_6$, wherein
$R_6$ is H or a $C_1$-$C_6$ alkyl group;
$R_3$ and $R_4$ are selected independently from H and $C_1$-$C_8$ alkyl or together with the nitrogen to which they are bound form a ring having 3 to 7 members;
its enantiomers or mixtures thereof, its solvates, hydrates, or salts,
which comprises:
a) reacting a compound of formula (IV)

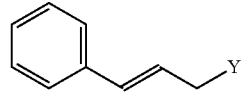

(IV)

wherein Y is a leaving group,
with a primary or secondary amine of formula (V)

(V)

wherein $R_3$ and $R_4$ are selected independently from hydrogen and linear or branched $C_1$-$C_8$ alkyl or together with the nitrogen to which they are bound form a ring having 3 to 7 members;
to obtain a compound of formula (II)

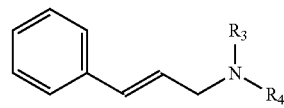

(II)

wherein $R_3$ and $R_4$ have the previously indicated meaning, b) reacting said compound of formula (II) with a compound of formula (III)

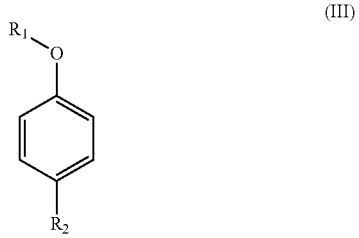

(III)

wherein $R_1$ and $R_2$ have the previously indicated meaning; and c) if desired, separating the desired (R) or (S) enantiomer, or the mixture of enantiomers, and/or converting the compound of formula (I) into a salt thereof.

Step a) of the method of the invention [2] corresponds to the step described above in relation to the method of obtaining the compound of formula (II), whereas steps b) and c) correspond to steps a) and b) of the method of the invention [1] and have been described above.

The compounds of formula (I) which can be obtained by means of the method of the invention [2], as well as their enantiomers or mixtures thereof, their solvates, hydrates, or salts, correspond to those described above in relation to the method of the invention [1], the content of which is considered to be reproduced.

The following examples illustrate the invention and must not be considered as limiting the scope thereof.

EXAMPLE 1

Obtaining N,N'-diisopropyl-3-phenyl-2-propenamine [Compound of Formula (II) wherein $R_3$ and $R_4$ are isopropyl]

A) From Cinnamyl Bromide

A solution of 10 g of cinnamyl bromide (0.05 moles, 1 equivalent) in 10 ml of ethanol is added, in a one hour interval, to a solution of 28.5 ml of diisopropylamine (0.2 moles, 4 equivalents) in 30 ml of ethanol heated at 30° C. After approximately one hour, the reaction is considered to be finished and the solvent and remains of diisopropylamine are removed by distillation at reduced pressure. 100 ml of toluene and 150 ml of water are incorporated to the residue and concentrated HCl is added until a pH between 1 and 2, the phases are separated; the aqueous phase is basified by adding sodium hydroxide until a pH between 10 and 11, is extracted 150 ml of heptane and washed with water. The organic extract is subjected to distillation at reduced pressure to give rise to an oil weighing 8.6 g (90% yield) corresponding to the product of the title.

$^{13}$C-NMR (CDCl$_3$, δ in ppm): 137.82 (C), 132.12 (CH), 130.17 (CH), 128.71 (CH), 127.17 (CH), 126.37 (CH), 48.46 (CH), 47.90 (CH$_2$) and 20.98 (CH$_3$)

B) From Cinnamyl Chloride

A solution of 73 ml of cinnamyl chloride (0.52 moles, 1 equivalent) in 80 ml of ethanol is added, in the interval of one hour, to a solution of 185 ml of diisopropylamine (1.30 moles, 2.5 equivalents) in 240 ml of ethanol heated at 50° C. The reaction is maintained for 7 hours at 50° C. and 14 hours at 60° C., considering to be finished and the solvent and remains of diisopropylamine are removed by distillation at reduced pressure. 160 ml of toluene and 240 ml of water are incorporated to the residue, concentrated HCl is added until a pH between 1 and 2, the phases are separated and the aqueous phase is basified by adding sodium hydroxide until a pH between 12 and 13, it is extracted with 250 ml of heptane and washed with water. The organic extract is subjected to distillation at reduced pressure to give rise to an oil weighing 76.71 g (67% yield) corresponding to the product of the title.

The product can be isolated as a hydrochloride by dissolving in ethanol and adding a solution of ClH(g) in ethanol, precipitating in the form of a white solid.

EXAMPLE 2

Obtaining N,N-diisopropyl-3-(2-hydroxy-5-methylphenyl)-3-phenylpropylamine [Compound of Formula (I) wherein $R_1$ is hydrogen, $R_2$ is methyl and $R_3$ and $R_4$ are isopropyl]

A) Using Aqueous Hydrobromic Acid (aq BrH)/Acetic Acid (AcOH)

5 g of N,N-diisopropyl-3-phenyl-2-propenamine (0.023 moles, 1 equivalent) and 6 g of p-cresol (0.055 moles, 2.4 equivalents) are incorporated to a solution of 13 ml of acetic acid. 15 ml of 48% HBr in water is added to the solution formed and it is heated until the reflux temperature. Once the reaction has ended, it is cooled and the solid formed is filtered, washing it with water. The obtained solid forms N,N-diisopropyl-3-(2-hydroxy-5-methylphenyl)-3-phenylpropylamine (tolterodine) in the form of raw hydrobromide, which can be recrystallized in ethanol, methanol or isopropanol to give purified N,N-diisopropyl-3-(2-hydroxy-5-methylphenyl)-3-phenylpropylamine hydrobromide.

Obtained amount of raw N,N-diisopropyl-3-(2-hydroxy-5-methylphenyl)-3-phenylpropylamine: 6.56 g.

Obtained amount of purified N,N-diisopropyl-3-(2-hydroxy-5-methylphenyl)-3-phenylpropylamine: 4.8 g.

The reaction can alternatively be carried out using 70% HClO$_4$ in water or aqueous sulfuric acid and heating at 100-110° C.

B) Using p-toluenesulfonic Acid TsOH/Acetic Acid (AcOH)

5 g of N,N-diisopropyl-3-phenyl-2-propenamine (0.023 moles, 1 equivalent) and 12 g of p-cresol (0.055 moles, 4.8 equivalents) are incorporated to a solution of acetic acid. 21.86 g of p-toluenesulfonic acid are added, in 30 minutes, to said solution, it is heated at 50° C. for 8 hours and finally at 100° C. until the end of the reaction. The volatile substances are distilled at reduced pressure and the reaction mixture is distributed between 100 ml of water and 100 ml of toluene, the suspension formed is taken to pH 9-10 and the organic phase is separated. The solvent is distilled at reduced pressure and the obtained reaction mass is purified by means of column chromatography, obtaining the product of the title in the form of an oil. 2 g of purified N,N-diisopropyl-3-(2-hydroxy-5-methylphenyl)-3-phenylpropylamine base.

EXAMPLE 3

Obtaining N,N-diisopropyl-3-(2-methoxy-5-methylphenyl)-3-phenylpropylamine [Compound of Formula (I) wherein $R_1$ and $R_2$ are methyl and $R_3$ and $R_4$ are isopropyl]

A) Using AlCl$_3$ 8 ml of anisole (0.065 moles, 8.2 equivalents) and 2 g of N,N-diisopropyl-3-phenyl-2-propenamine hydrochloride and incorporated to a 50 ml flask. 2.1 g of AlCl$_3$ (0.0157 moles, 2 equivalents) are added to the cooled reaction mixture, taking care of the exothermy, without the temperature exceeding 40° C. The obtained suspension is heated until reaching 40° C. and is maintained in this way for 15-30 hours, until the reaction is considered to be finished. The majority presence of N,N-diisopropyl-3-(2-methoxy-5-methylphenyl)-3-phenylpropylamine together with N,N-diisopropyl-3-(2-hydroxy-5-methylphenyl)-3-phenylpropylamine as the main impurity is observed by high performance liquid chromatography (HPLC). The reaction mixture is treated by adding 60 ml of water and extracting with 100 ml of dichloromethane. Another 100 ml of water is added to the organic extract and it is neutralized until pH 9-10, the phases are separated and the organic phase is saved. The solvent is removed at reduced pressure and the obtained residue consisting of excess anisole and the product of the title (mainly) is passed through a chromatographic column, the product of the title being isolated as an oil.

B) Using Sulfuric Acid 46.8 ml of anisole (0.367 moles, 4 equivalents) and 18 ml of water are added to a round-bottom flask. The obtained suspension is cooled in an ice/water bath and 24.8 ml of 98% sulfuric acid are loaded, taking approximately 30 minutes, controlling that the temperature is below 40° C. The reaction mixture is heated to 100° C., and at this temperature 20 g of N,N-diisopropyl-3-phenyl-2-propenamine in the form of a base are added, taking at least 30 minutes. The progress of the reaction is monitored by HPLC until its end in approximately 1-4 hours. Once it has ended, 150 ml of water and 150 ml of toluene are added, the product being in the aqueous phase and the anisole being in the organic phase. The separated anisole-free aqueous phase is neutralized until pH 12-13 and extracted with 150 ml of heptane. The organic phase is distilled at reduced pressure and is changed for ethyl acetate, BrH in acetic acid is added dropwise to the solution, N,N-diisopropyl-3-(2-methoxy-5-methylphenyl)-3-phenylpropylamine in the form of hydrobromide precipitating, which can be filtered and washed with more ethyl acetate. The mother liquors are neutralized and passed through a chromatographic column to obtain a second fraction of the product of the title in the form of an oil. Approximate yield: 50%.

C) Using Perchloric Acid 11.7 ml of anisole (0.092 moles, 4 equivalents) and 1.5 ml of water are introduced in a round-bottom flask. 9.9 ml of 70% perchloric acid are added dropwise to this mixture, cooled in an ice bath, taking about 30 minutes. The reaction mixture is heated at 80° C. and the addition of 5 g of N,N-diisopropyl-3-phenyl-2-propenamine is started, taking about 30 minutes. The reaction is followed by HPLC in one hour intervals; after 5-6 hours, the peak corresponding to the product of the title is observed as a major peak (purity greater than 80% once the excess anisole has been subtracted).

EXAMPLE 4

Obtaining (R)-(+)-N,N-diisopropyl-3-(2-methoxy-5-methylphenyl)-3-phenylpropylamine tartrate [Compound of Formula (I) wherein $R_1$ and $R_2$ are methyl and $R_3$ and $R_4$ are isopropyl]

5.2 ml of NaOH (50%) are added to a suspension of N,N-diisopropyl-3-(2-methoxy-5-methylphenyl)-3-phenylpropylamine hydrobromide (53 g, 0.131 moles) in 750 ml of $CH_2Cl_2$ and 375 ml of water, adjusting the pH to 9.5 with acetic acid if necessary. Once this pH is reached, it is maintained stirring for 45 minutes and it is extracted with $CH_2Cl_2$, obtaining 42.55 g of the free amine. A solution of 29.43 g of L-tartaric acid dissolved in 280 ml of ethanol at 60° C. is then added to said amine dissolved in 140 ml of ethanol, at 60° C. The reaction is maintained at a temperature comprised between 60° C. and 70° C. for 1 hour and it is slowly cooled until 0° C., maintaining it at said temperature for another hour. The resulting white precipitate is filtered and vacuum-dried for 14 hours, obtaining 31.08 g of product. 1,200 ml of ethanol are then mixed with the 31.08 g of obtained product and it is heated at 80° C. for 30 minutes; the volume of ethanol is concentrated to half by distillation and it is gradually cooled at room temperature and subsequently for 1 hour at 0° C. (R)-tolterodine L-tartrate is obtained by filtration and vacuum-dried at 60° C. for 14 hours, obtaining 27.51 g of product. This method is repeated on a second occasion with the 27.51 g of recrystallized (R)-tolterodine L-tartrate to give 22.23 g with a purity of 99.80% of the optically active compound.

The invention claimed is:

1. A method of obtaining a 3,3-diphenylpropylamine of formula (I):

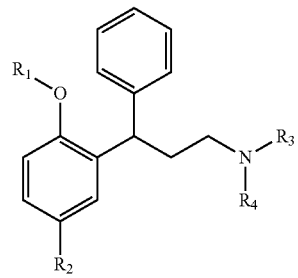

(I)

wherein
  $R_1$ is hydrogen, $C_1$-$C_6$ alkyl, $C_1$-$C_6$ haloalkyl or alkoxyalkyl of formula —$(CH_2)_n$—O—$R_5$, wherein n is an integer of 1 to 3 and $R_5$ is $C_1$-$C_6$ alkyl;
  $R_2$ is $C_1$-$C_6$ alkyl, $C_1$-$C_6$ alkoxy, halogen, $NO_2$, CN, CHO which may be free or protected, $CH_2OH$ or $COOR_6$, wherein $R_6$ is H or a $C_1$-$C_6$ alkyl group;
  $R_3$ and $R_4$ are selected independently from H and $C_1$-$C_8$ alkyl or together with the nitrogen to which they are bound form a ring having 3 to 7 members;
its enantiomers or mixtures thereof, or its salts,
  which comprises:
  a) reacting a compound of formula (II)

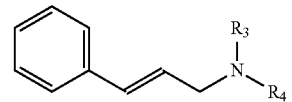

(II)

wherein $R_3$ and $R_4$ have the previously indicated meaning, with a compound of formula (III)

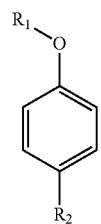

(III)

wherein $R_1$ and $R_2$ have the previously indicated meaning; and b) optionally, separating the desired (R) or (S) enantiomer, or the mixture of enantiomers, and/or converting the compound of formula (I) into a salt thereof.

2. A method according to claim 1, wherein the reaction of the compound of formula (II) with the compound of formula (III) is carried out in a reaction medium comprising an acid.

3. A method according to claim 2, wherein said acid is an inorganic acid.

4. A method according to claim 3, wherein said inorganic acid is selected from hydrobromic acid, perchloric acid, sulfuric acid, hydrochloric acid, phosphoric acid and mixtures thereof.

5. A method according to claim 2, wherein said acid is an organic acid.

6. A method according to claim 5, wherein said organic acid is selected from p-toluenesulfonic acid, methanesulfonic acid, acetic acid, trifluoroacetic acid, and mixtures thereof.

7. A method according to claim 2, wherein said reaction medium comprises one or more inorganic acids and one or more organic acids.

8. A method according to claim 7, wherein said reaction medium comprises an inorganic acid selected from the group consisting of hydrobromic acid, perchloric acid, sulfuric acid, hydrochloric acid, phosphoric acid and mixtures thereof and an organic acid.

9. A method according to claim 2, wherein said acid is a Lewis acid.

10. A method according to claim 9, wherein said Lewis acid is $AlCl_3$, $SnCl_4$, $ZnCl_2$, $BF_3$, or mixtures thereof.

11. A method according to claim 1, wherein in the obtained compound of formula (I) $R_1$ is H or methyl, $R_2$ is methyl and $R_3$ and $R_4$ are both isopropyl, or a salt thereof.

12. A method according to claim 1, wherein the obtained compound of formula (I) is (R)-(+)-N,N-diisopropyl-3-(2-methoxy-5-methylphenyl)-3-phenylpropylamine or a salt thereof.

13. A method according to claim 12, wherein the obtained compound of formula (I) is (R)-(+)-N,N-diisopropyl-3-(2-methoxy-5-methylphenyl)-3-phenylpropylamine hydrobromide or (R)-(+)-N,N-diisopropyl-3-(2-methoxy-5-methylphenyl)-3-phenylpropylamine tartrate.

14. A method of obtaining a 3,3-diphenylpropylamine of formula (I')

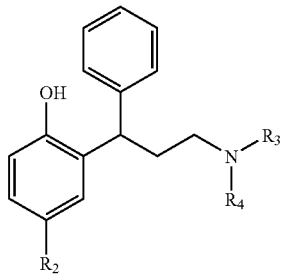

(I')

wherein
$R_2$ is $C_1$-$C_6$ alkyl, $C_1$-$C_6$ alkoxy, halogen, $NO_2$, CN, CHO which may be free or protected, $CH_2OH$ or $COOR_6$, wherein $R_6$ is H or $C_1$-$C_6$ alkyl;
$R_3$ and $R_4$ are selected independently from H, $C_1$-$C_8$ alkyl, or together with the nitrogen to which they are bound form a ring having 3 to 7 members;
its enantiomers or mixtures thereof, or its salts, which comprises:
a) reacting a compound of formula (II)

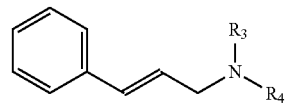

(II)

wherein $R_3$ and $R_4$ have the previously indicated meaning, with a compound of formula (III')

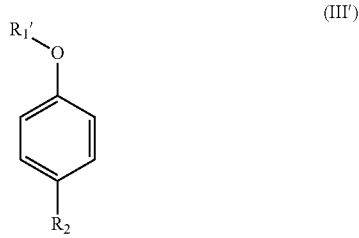

(III')

wherein $R'_1$ is $C_1$-$C_6$ alkyl, $C_1$-$C_6$ haloalkyl or alkoxyalkyl of formula $—(CH_2)_n—O—R_5$, wherein n is an integer of 1 to 3 and $R_5$ is $C_1$-$C_6$ alkyl; and $R_2$ has the previously indicated meaning,
to give rise to a compound of formula (I"):

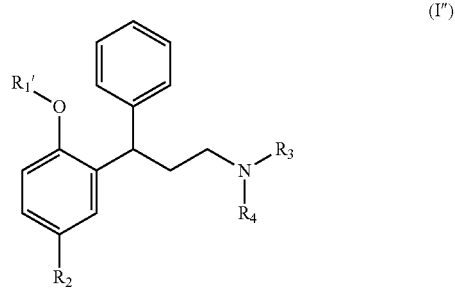

(I")

wherein $R'_1$, $R_2$, $R_3$ and $R_4$ have the previously indicated meaning;

b) transforming $R'_1$ into hydrogen to obtain the compound of formula (I'); and c) optionally, separating the desired (R) or (S) enantiomer, or the mixture of enantiomers, and/or converting the compound of formula (I') into a salt thereof.

15. A method according to claim 14, wherein the reaction of the compound of formula (II) with the compound of formula (III') is carried out in a reaction medium comprising an acid.

16. A method according to claim 15, wherein said acid is an inorganic acid other than hydrobromic acid.

17. A method according to claim 16, wherein said inorganic acid is selected from perchloric acid, sulfuric acid, and mixtures thereof.

18. A method according to claim 15, wherein said acid is an organic acid.

19. A method according to claim 18, wherein said organic acid is selected from p-toluenesulfonic acid, methanesulfonic acid, acetic acid, trifluoroacetic acid, and mixtures thereof.

20. A method according to claim 15, wherein said reaction medium comprises one or more inorganic acids other than hydrobromic acid and one or more organic acids.

21. A method according to claim 20, wherein said reaction medium comprises an inorganic acid selected from the group consisting of perchloric acid, sulfuric acid and mixtures thereof and an organic acid.

22. A method according to claim 15, wherein said acid is a Lewis acid.

23. A method according to claim 22, wherein said Lewis acid is $AlCl_3$, $SnCl_4$, $ZnCl_2$, $BF_3$, or mixtures thereof.

24. A method according to claim 14, wherein in the obtained compound of formula (I') $R_2$ is methyl and $R_3$ and $R_4$ are both isopropyl, or a salt thereof.

25. A method according to claim 14, wherein the obtained compound of formula (I') is (R)-(+)-N,N-diisopropyl-3-(2-methoxy-5-methylphenyl)-3-phenylpropylamine or a salt thereof.

26. A method according to claim 25, wherein the obtained compound of formula (I') is (R)-(+)-N,N-diisopropyl-3-(2-methoxy-5-methylphenyl)-3-phenylpropylamine hydrobromide or (R)-(+)-N,N-diisopropyl-3-(2-methoxy-5-methylphenyl)-3-phenylpropylamine tartrate.

27. A method of obtaining a 3,3-diphenylpropylamine of formula (I):

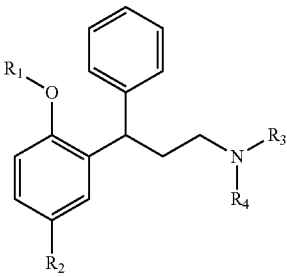

(I)

wherein
- $R_1$ is hydrogen, $C_1$-$C_6$ alkyl, $C_1$-$C_6$ haloalkyl or alkoxyalkyl of formula —$(CH_2)_n$—O—$R_5$, wherein n is an integer of 1 to 3 and $R_5$ is $C_1$-$C_6$ alkyl;
- $R_2$ is $C_1$-$C_6$ alkyl, $C_1$-$C_6$ alkoxy, halogen, $NO_2$, CN, CHO which may be free or protected, $CH_2OH$ or $COOR_6$, wherein $R_6$ is H or $C_1$-$C_6$ alkyl;
- $R_3$ and $R_4$ are selected independently from H and $C_1$-$C_8$ alkyl or together with the nitrogen to which they are bound form a ring having 3 to 7 members;

its enantiomers or mixtures thereof, or its salts,
which comprises:
a) reacting a compound of formula (IV)

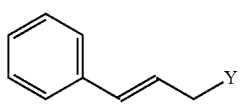

(IV)

wherein Y is a leaving group,
with a primary or secondary amine of formula (V)

(V)

wherein $R_3$ and $R_4$ are selected independently from hydrogen and linear or branched $C_1$-$C_8$ alkyl or together with the nitrogen to which they are bound form a ring having 3 to 7 members;
to obtain a compound of formula (II)

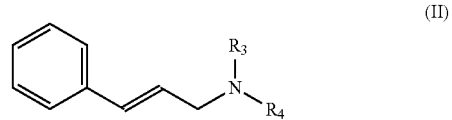

(II)

wherein $R_3$ and $R_4$ have the previously indicated meaning,
b) reacting said compound of formula (II) with a compound of formula (III)

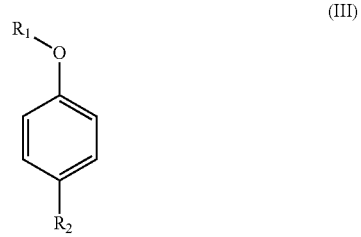

(III)

wherein $R_1$ and $R_2$ have the previously indicated meaning; and
c) optionally, separating the desired (R) or (S) enantiomer, or the mixture of enantiomers, and/or converting the compound of formula (I) into a salt thereof.

28. A method according to claim 27, wherein in the obtained compound of formula (I) $R_1$ is H or methyl, $R_2$ is methyl and $R_3$ and $R_4$ are both isopropyl, or a salt thereof.

29. A method according to claim 27, wherein the obtained compound of formula (I) is (R)-(+)-N,N-diisopropyl-3-(2-methoxy-5-methylphenyl)-3-phenylpropylamine or a salt thereof.

30. A method according to claim 27, wherein the obtained compound of formula (I) is (R)-(+)-N,N-diisopropyl-3-(2-methoxy-5-methylphenyl)-3-phenylpropylamine hydrobromide or (R)-(+)-N,N-diisopropyl-3-(2-methoxy-5-methylphenyl)-3-phenylpropylamine tartrate.

31. A method according to claim 7, wherein said reaction medium comprises an inorganic acid selected from the group consisting of hydrobromic acid, perchloric acid, sulfuric acid, hydrochloric acid, phosphoric acid and mixtures thereof and acetic acid.

32. A method according to claim 20, wherein said reaction medium comprises an inorganic acid selected from the group consisting of perchloric acid, sulfuric acid and mixtures thereof and acetic acid.

* * * * *